(12) United States Patent
Juttu et al.

(10) Patent No.: US 6,784,333 B2
(45) Date of Patent: Aug. 31, 2004

(54) CATALYST FOR AROMATIZATION OF ALKANES, PROCESS OF MAKING AND USING THEREOF

(75) Inventors: Gopalakrishnan G. Juttu, Sugar Land, TX (US); Robert Scott Smith, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 16 days.

(21) Appl. No.: 10/213,313

(22) Filed: Aug. 6, 2002

(65) Prior Publication Data

US 2004/0028584 A1 Feb. 12, 2004

(51) Int. Cl.$^7$ ............................. C07C 15/00; C07C 2/52
(52) U.S. Cl. ..................... 585/419; 585/407; 585/418
(58) Field of Search ................................ 585/407, 418, 585/419

(56) References Cited

U.S. PATENT DOCUMENTS

| | | | |
|---|---|---|---|
| 3,329,480 A | 7/1967 | Young | |
| 3,329,481 A | 7/1967 | Young | |
| 4,036,741 A | 7/1977 | Pollitzer et al. | |
| 4,208,305 A | 6/1980 | Kouwenhoven et al. | |
| 4,590,322 A | * 5/1986 | Chu ........................... | 585/415 |
| 4,590,323 A | * 5/1986 | Chu ........................... | 585/417 |
| 4,704,494 A | 11/1987 | Inui | |
| 4,705,907 A | * 11/1987 | Inui ........................... | 585/415 |
| 4,713,227 A | 12/1987 | Derouane et al. | |
| 4,836,336 A | 6/1989 | Schroder | |
| 4,910,357 A | 3/1990 | Dessau et al. | |
| 5,124,497 A | 6/1992 | Dessau et al. | |
| 5,179,054 A | 1/1993 | Schipper et al. | |
| 5,227,557 A | 7/1993 | Bournonville et al. | |
| 5,371,307 A | * 12/1994 | Guth et al. ................. | 585/250 |
| 5,456,822 A | 10/1995 | Marcilly et al. | |
| 6,160,191 A | 12/2000 | Smith et al. | |
| 6,315,892 B1 | 11/2001 | Le Peltier et al. | |

FOREIGN PATENT DOCUMENTS

JP    59-121115    7/1984

OTHER PUBLICATIONS

D. W. Breck, Zeolite Molecular Sieves, p. 320–331, John Wiley & Sons (1974).
T. Komatsu et al, "Aromatization of butane on Pt–Ge intermetallic compounds supported on HZSM–5", 2000. Applied Catalysis A: General, vol. 194–195, p. 333–339 (2000).
"Synthesis and Characterization of Ge–ZSM–5 Zeolites", H. Kosslick et al., J. Phys.Chem., vol. 97, p. 5678–5684 (1993).
"EXAFS Study of Germanium–rich MFI–Type Zeolites", M.H. Tuilier et al., Zeolites, vol. 11, p. 662–665 (Sep./Oct., 1991).
"Propane Transformation over H–ZSM–5 Zeolite Modified with Germanium", C.C. Salguero et al., Catalysis Letters, vol. 47, p. 143–154 (1997).

* cited by examiner

Primary Examiner—Tom Dunn
Assistant Examiner—Christina Ildebrando
(74) Attorney, Agent, or Firm—Jim Wheelington

(57) ABSTRACT

A catalyst, a process for making the catalyst and a process for using the catalyst in aromatization of alkanes to aromatics, specifically, aromatization of alkanes having two to six carbon atoms per molecule, such as propane, to aromatics, such as benzene, toluene and xylene. The catalyst is an aluminum-silicon-germanium zeolite on which platinum has been deposited. Germanium is in the framework of the crystalline zeolite. Platinum is deposited on the zeolite. The catalyst may be supported on magnesia, alumina, titania, zirconia, thoria, silica, boria or mixtures thereof. The catalyst may contain a sulfur compound on the surface of the catalyst. The sulfur compound may be added to the catalyst in a pretreatment process or introduced with the hydrocarbon feed to contact the catalyst during the aromatization process. Generally, the catalyst may be of the formula $M[(SiO_2)(XO_2)_x(YO_2)_y]Z^+_{y/n}$ where M is a noble metal such as platinum or gold, X is titanium, germanium, tin or another tetravalent element, Y is boron, aluminum, gallium, indium, tellurium or another trivalent element, Z is a cation with a valence of n such as $H^+$, $Na^+$, $K^+$, $Rb^+$, $Cs^+$, $Ca^{2+}$, $Mg^{2+}$, $Sr^{2+}$ or $Ba^{2+}$, x varies from 0–0.15 and y is 0–0.125. An example catalyst would be represented as $[H^+Pt[[Si_{91}Ge_4Al_1O_{192}]$-MFI.

16 Claims, 1 Drawing Sheet

CATALYST FOR AROMATIZATION OF ALKANES, PROCESS OF MAKING AND USING THEREOF

BACKGROUND OF THE INVENTION

1. Field of the Invention

This invention relates to a catalyst for the aromatization of alkanes to aromatics, specifically a zeolite, preferably a MFI-type structure, most preferably a ZSM-5 MFI zeolite, catalyst for the aromatization of alkanes having two to six carbon atoms per molecule to aromatics, such as benzene, toluene and xylene.

2. Description of the Prior Art

Zeolite is a crystalline hydrated aluminosilicate that may also contain other metals, such as sodium, calcium, barium, and potassium, and that has ion exchange properties (Encarta® World English Dictionary [North American Edition] © & (P) 2001 Microsoft Corporation). A method for preparing a zeolite comprises (a) preparing an aqueous mixture of silicon oxide and sources of oxides of aluminum; and (b) maintaining said aqueous mixture under crystallization conditions until crystals of said zeolite form. Much zeolite research has focused on the synthesis of zeolite frameworks containing elements other than silicon and aluminum.

U.S. Pat. No. 6,160,191 discloses that the term "zeolite" includes not only aluminosilicates but substances in which the aluminum is replaced by gallium, titanium, iron or boron and substances in which silicon is replaced by germanium, tin and phosphorous. U.S. Pat. Nos. 3,329,480 and 3,329,481, both issued to D. A. Young, report the existence of crystalline zirconosilicate and titanosilicate zeolites. A zeolite having chromium in the tetrahedral positions has been described by Yermolenko et al at the Second Oil Union Conference on Zeolites, Leningrad, 1964, pages 171–8 (published 1965). However, D. W. Breck, in Zeolite Molecular Sieves, p. 322, John Wiley & Sons (1974) suggests that the chromium present was not present in a zeolite A structure and furthermore was present as an impurity in insoluble form. The impurity was said to be in the form of a chromium silicate as confirmed by the nature of the water vapor adsorption isotherm.

The zeolite ZSM-5 has been synthesized with many elements other than Al in the framework, including iron. Synthesis of an iron-containing zeolitic structure was reported in Japanese Kokai 59,121,115, published Jul. 13, 1984, which disclosed an aluminosilicate having a faujasite structure and containing coordinated iron. The chemical composition is said to be of the formula $aM_{2/n}O:bFe_2O_3:Al_2O_3:cSiO_2$ where M can be H, alkali metal or alkaline earth metal; the symbol n is the valence of M; a=1+/−0.3; c is between 4.6 and 100; and a is less than b and both are less than 7. The crystal lattice parameter $a_o$ is between 24.3 and 24.7 angstroms. Similarly, U.S. Pat. No. 4,208,305 discloses crystalline silicates which are structurally a three-dimensional network of $SiO_4^{2-}$, $FeO_4^{2-}$ and, optionally, $AlO_4^-$, $GaO_4^-$ and $GeO_4^-$ tetrahedrons, which are interlinked by common oxygen atoms and are of the overall composition in dehydrated form:

where R is a cation; $a \geq 0.1$; $b \geq 0$; $c \geq 0$; $a+b+c=1$; $y \geq 10$; $d \geq 0.1$; $e \geq 0$; $d+e=1$; and n is the valence of R. Silicates not containing gallium, germanium and aluminum are preferred. Silicates of a particular X-ray powder diffraction pattern are also preferred.

U.S. Pat. No. 4,713,227 discloses crystalline metalloaluminophosphates having microposity, catalytic activity and ion-exchange properties which contain metals such as arsenic, bismuth, cobalt, iron, germanium, manganese, vanadium and antimony within the framework.

U.S. Pat. No. 5,179,054 states that although matrices may be formed with the germanium analog of silicon, these are expensive and generally no better than the metallosilicates, i.e., aluminosilicate, gallosilicate, ferrosilicate and borosilicate, for the molecular sieve component of a catalyst for catalytic cracking of heavy hydrocarbon oils to produce hydrocarbons boiling in the gasoline and distillate range.

In the publication "Aromatization of butane on Pt—Ge intermetallic compounds supported on HZSM-5" by T. Komatsu et al in Applied Catalysis A: General, vol. 194–195, p. 333–339 (2000) platinum-germanium intermetallic species, platinum species and germanium species were deposited on HZSM-5 for catalysts to convert butane to aromatics. The Pt—Ge intermetallic catalyst was reported to have a more stable time on stream for conversion and selectivity than that of the Pt catalyst. Catalysts with large amount of germanium relative to platinum were reported to have lower conversion of butane and lower selectivity to aromatics.

U.S. Pat. No. 4,704,494 discloses a process for conversion of low molecular paraffin hydrocarbons to aromatic hydrocarbons using a platinum- or gallium-modified metallosilicate (Si/Me) catalyst where Me is aluminum, gallium, titanium, zirconium, germanium, lanthanum, manganese, chromium, scandium, vanadium, iron, tungsten, molybdenum, nickel or a mixture thereof. The working examples were prepared with Me being aluminum or gallium. No example with germanium was prepared. There was no suggestion to select germanium over any of the other elements or mixtures of elements.

U.S. Pat. No. 5,456,822 discloses a process for aromatization of hydrocarbons containing two to nine carbon atoms per molecule with a catalyst containing an MFI zeolite having silicon, aluminum and/or gallium in the framework, a matrix, and gallium, a noble metal of the platinum family and a metal selected from tin, germanium, indium, copper, iron, molybdenum, gallium, thallium, gold, silver, ruthenium, chromium, tungsten and lead deposited on the zeolite. No example with germanium was prepared. There was no suggestion to select germanium over any of the other elements or mixtures of elements.

U.S. Pat. Nos. 4,910,357 and 5,124,497 disclose a process for producing monosubstituted monoalkylaromatics from $C_8$, paraffins using a nonacid platinum-containing catalyst in which the crystalline material contains tin, indium, thallium or lead. These catalysts provided much higher selectivity to aromatics than other platinum catalysts incorporating other elements in the crystalline material, including germanium.

U.S. Pat. No. 6,315,892 discloses a process for making a catalyst of a carrier, platinum and germanium wherein the germanium is introduced as an organic compound which is contacted with the precatalyst in the reaction zone.

U.S. Pat. No. 5,227,557 discloses a process for the aromatization of hydrocarbons containing 2 to 4 carbon atoms per molecule using an MFI zeolite catalyst containing platinum and one metal chosen from tin, germanium, lead and indium. Both platinum and the additional metal can be introduced on the MFI zeolite by impregnation, exchange or other known methods. The working examples used impregnation for both platinum and the additional metal. Example E contained 0.3% platinum and 0.2% germanium.

U.S. Pat. No. 4,036,741 discloses a process for converting hydrocarbons (including dehydrocyclization of paraffins to aromatics) with an acidic catalyst of a porous carrier material containing halogen along with platinum, cobalt and germanium uniformly dispersed throughout the carrier material which may be a crystalline zeolitic aluminosilicate. The catalyst was tested as a reforming catalyst for a relatively low-octane gasoline fraction under substantially sulfur-free conditions against a catalyst containing platinum and germanium but without cobalt. The results indicated that cobalt was essential for better activity and activity stability.

Some zeolite catalysts containing a Group VIII metal are susceptible to sulfur poisoning. For some platinum catalysts, despite some sensitivity to sulfur, modest amounts of sulfur, such as 10 to 100 ppm, are acceptable and sometimes preferred. A standard sulfurization method that is well known in the art consists in heating in the presence of hydrogen sulfide or a mixture of hydrogen sulfide and hydrogen or nitrogen to a temperature of between 150 and 800° C., preferably between 250 and 600° C.

U.S. Pat. No. 4,836,336 discloses a process for converting $C_6$–$C_{12}$ paraffinic hydrocarbon feed to aromatics using a noble metal low acidity medium pore size zeolite catalyst. The noble metal is preferably a platinum group metal (platinum, palladium, iridium, osmium, rhodium or ruthenium) and the zeolite is preferably ZSM-5, ZSM-11, ZSM-12, ZSM-22, ZSM-23, ZSM-35, ZSM-38, ZSM-48 or Zeolite Beta. The noble metal is modified to its sulfide form by presulfiding the catalyst with $H_2S$, $SO_2$ or an organic sulfur compound to increase aromatic selectivity of the catalyst. Germanium is not disclosed as a component of the catalyst.

It would be advantageous to have a zeolite-type catalyst which maintained relatively constant selectivity for conversion of lower alkanes to aromatics, such as benzene, toluene and xylene, over a period of time on stream.

OBJECTS OF THE INVENTION

Accordingly, an object of this invention is to provide an aluminum-silicon-germanium zeolite on which platinum has been deposited, said catalyst having relatively constant selectivity for conversion of lower alkanes to aromatics.

And, an object of this invention is to provide a, process for synthesizing a catalyst of an aluminum-silicon-germanium zeolite on which platinum has been deposited.

Also, an object of this invention is to provide a process for the aromatization of hydrocarbons using a catalyst of an aluminum-silicon-germanium zeolite on which platinum has been deposited.

Further, an object of this invention is to provide a process for pretreating a catalyst for aromatization of hydrocarbons of an aluminum-silicon-germanium zeolite on which platinum has been deposited.

SUMMARY OF THE INVENTION

These and other objects are accomplished by a microporous aluminum-silicon-germanium zeolite on which platinum has been deposited. The catalyst is synthesized by preparing a zeolite containing aluminum, silicon and germanium in the framework, depositing platinum on the zeolite and calcining the zeolite. The zeolite structure may be of MFI, FAU, TON, MFL, VPI, MEL, AEL, AFI, MWW or MOR, but preferably, the zeolite has a MFI structure, more preferably is ZSM-5 MFI zeolite. The catalyst is used in a process for aromatization of alkanes by contacting the microporous aluminum-silicon-germanium zeolite on which platinum has been deposited with at least one alkane at aromatization conditions and recovering the aromatic product.

BRIEF DESCRIPTION OF THE DRAWINGS

A more complete appreciation of the invention and many of the attendant advantages thereof will be readily understood by reference to the following detailed description when considered in connection with the accompanying drawings.

DETAILED DESCRIPTION OF THE INVENTION

Figure 1:
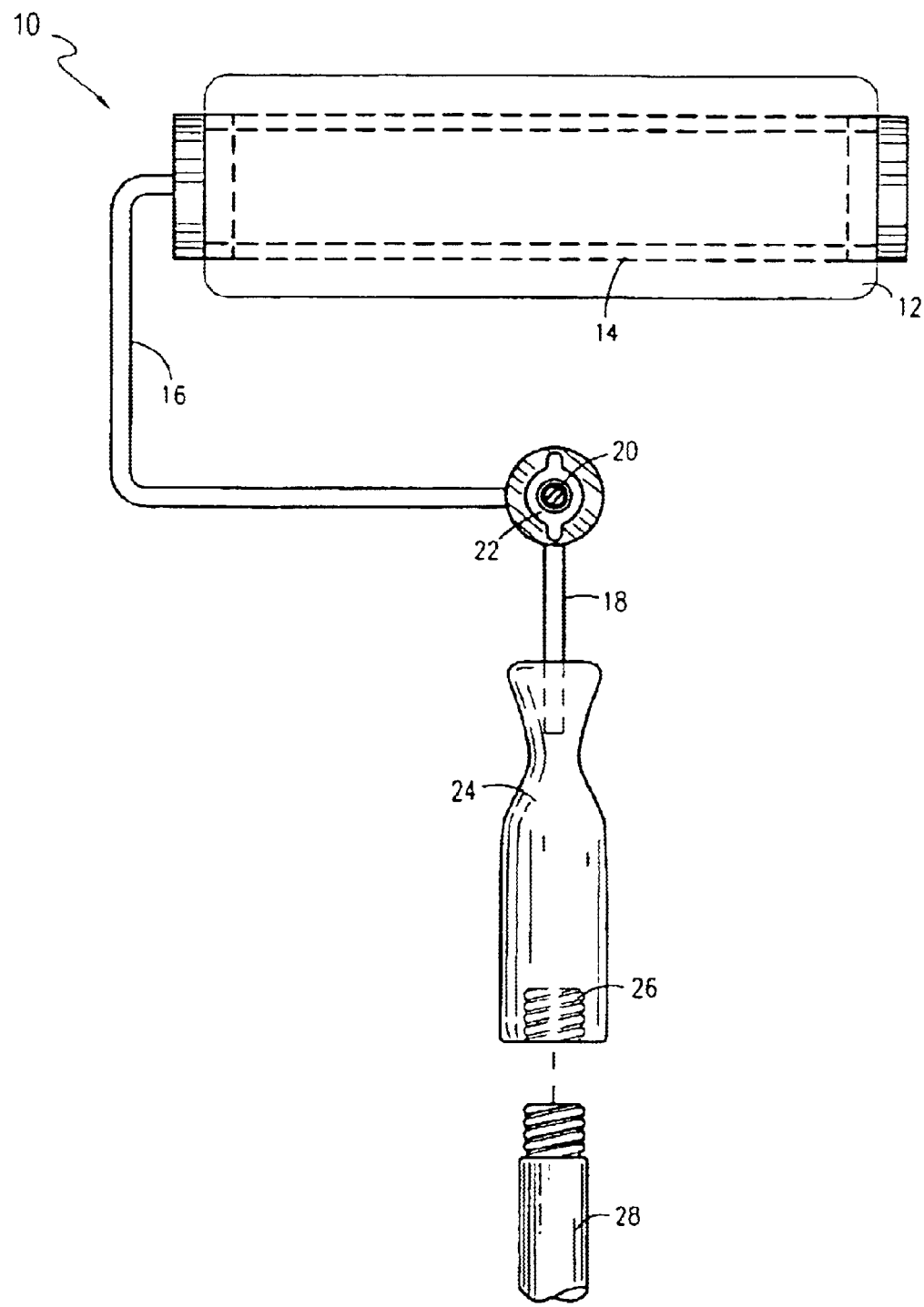
FIG. 1 is a graph showing the percent conversion or selectivity of a catalyst of the present invention related to time on stream in minutes.

Depositing platinum on a MFI zeolite catalyst precursor in which germanium has been introduced into the aluminosilicate framework of the zeolite has been found to produce a catalyst that has increased stability with time on stream, i.e., maintains relatively constant selectivity for lower alkanes to aromatics, e.g., alkanes having two to six carbon atoms per molecule to benzene, toluene and xylene.

The zeolite can be prepared by any known method of preparing a MFI structure of aluminum, silicon and germanium. Zeolites are known to be crystallized silicates and include structures of $TO_4$ tetrahedra, which form a three dimensional network by sharing oxygen atoms where T represents tetravalent silicon and trivalent aluminum. Trivalent elements such as gallium and, more rarely, boron or beryllium may be substituted for the aluminum.

Zeolites generally crystallize from an aqueous solution. The typical technique for synthesizing zeolites comprises converting an amorphous gel to zeolite crystals by a hydrothermal process, employing a dissolution/recrystallization mechanism. The reaction medium also contains structuring agents which are incorporated in the microporous space of the zeolite network during crystallization, thus controlling the construction of the network and assisting to stabilize the structure through the interactions with the zeolite components.

As disclosed in U.S. Pat. No. 5,246,688, hereby incorporated by reference, MFI zeolites based on silicon oxide and, optionally, the oxides of titanium, germanium, zirconium and/or tin, are produced by (1) heating an aqueous, homogeneous reaction mixture which comprises (a) an $M_{2/n}$ $SiF_6$ complex, wherein M is a cation of valency n, and, optionally, at least one $M_{2/n}$ $TF_6$ complex, wherein T' is titanium, zirconium, germanium and/or tin, (b) a reagent providing OH ions by hydrothermal decomposition and a structuring agent (c), e.g., a tertiary amine or a quaternary ammonium compound, whereby a zeolite precipitate is formed therein, and (2) separating and calcining such precipitate to eliminate structuring agent from the pores and channels of the resulting zeolite.

Methods of preparation of a MFI zeolite can also be found in U.S. Pat. No. 3,702,886 and in J. Phys. Chem, vol. 97, p. 5678–5684 (1993), hereby incorporated by reference.

The silicon/germanium to aluminum atomic ratio (Si—Ge:Al) of the MFI zeolite is preferably greater than 25:1, more preferably in the range from 45:1 to 250:1, and most preferably in the range from 50:1 to 100:1. The silica to germania ratio is present preferably in the range from 100:1 to 8:1, more preferably in the range from 50:1 to 10:1 and most preferably in the range from 25:1 to 11:1.

Platinum is deposited on the MFI zeolite by any known method of depositing a metal on a zeolite. Typical methods of depositing a metal on zeolite are ion exchange and impregnation. Platinum is present preferably in the range from 0.05% to 3%, more preferably in the range from 0.2% to 2% and most preferably in the range from 0.2 to 1.5%.

The catalyst may be bound by oxides of magnesium, aluminum, titanium, zirconium, thorium, silicon, boron and mixtures thereof. Preferably, the support is amorphous and is an oxide of aluminum (alumina).

The catalyst preferably has average pore size preferably in the range from 5 angstroms to 100 angstroms, more preferably in the range from 5 angstroms to 50 angstroms and most preferably in the microporous range from 5 angstroms to 20 angstroms.

The catalyst may contain a reaction product, such as platinum sulfide, that is formed by contact of an element or compound deposited on the surface of the catalyst with a sulfur compound. Non-limiting examples of sulfur compounds are $H_2S$, $CnH_{2n+2}S$ where n=1–20, $C_nH_{2n+1}S_2$ where n=2–22 and $C_nH_{2n+1}S$ where n=2–22. The sulfur compound may be added before or during the aromatization reactions of light alkanes, i.e., the catalyst may be pretreated with the sulfur compound or the sulfur compound may be introduced with the hydrocarbon feed when it contacts the catalyst during the aromatization process. The amount of sulfur on the catalyst is preferably in the range of from 10 ppm to 0.1 wt. %.

The chemical formula of the catalyst may be represented as:

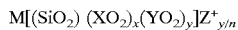

$$M[(SiO_2)\ (XO_2)_x(YO_2)_y]Z^+_{y/n}$$

where M is a noble metal such as platinum or gold, X is titanium, germanium, tin or another tetravalent element, Y is boron, aluminum, gallium, indium, tellurium or another trivalent element, Z is a cation with a valence of n such as $H^+$, $Na^+$, $K^+$, $Rb^+$, $Cs^+$, $Ca^{2+}$, $Mg^{2+}$, $Sr^{2+}$ or $Ba^{2+}$, x varies from 0–0.15 and y is 0–0.125. According to the IUPAC recommendations, an example catalyst would be represented as:

$$|H^+Pt|[Si_{91}Ge_4Al_1O_{192}]\text{-MFI}$$

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

Zeolite Synthesis:

40.6 g of colloidal silica (40% $SiO_2$), 2.251 g of aluminum nitrate [$Al(NO_3)_3 \cdot 9H_2O$], 19.575 g of TPAB, 14.7 g of hydrogen fluoride (40% aqueous solution), 91.3 g of methylamine (40% aqueous solution) and 39.54 g of water were mixed for twenty minutes. 3.93 g of germanium tetrachloride were added dropwise to the mixture while stirring. The pH was adjusted to approximately 10 by adding hydrogen fluoride (40% concentration). The mixture was stirred for 5 minutes. 175 g of the mixture were transferred to an autoclave reactor and heated at 170° C. for eighteen hours. The resulting solids were washed and dried at 90° C. overnight and then calcined by heating from room temperature to 550° C. at 1° per minute and maintaining the temperature at 550° C. for five hours. The final weight of the product was 13.6 g.

Forming 10.4 g of the zeolite synthesized above was combined with 14.9 g of hydrated $Al_2O_3$ and mixed. The mixture was wetted with 0.05N nitric acid to form a dough which was kneaded for fifteen minutes. The dough was dried overnight at 90° C. and then calcined at 550° C. for five hours. The resulting solid was crushed and sieved to form a 20/40 (U.S. mesh) powder.

The sieved powder from above was combined with approximately 125 mL of 1.0M ammonium nitrate. The pH was adjusted to 6 with 0.05 N nitric acid. The resulting mixture was placed in an oven at 60° C. for one hour, swirling occasionally. The mixture was decanted and the resulting solid was washed for thirty minutes with five aliquots of 60 mL distilled water at 60° C.

Optionally, the solid was dried overnight at 90° C.

Platinum Ion Exchange:

1.94 g of $(NH_3)_4Pt(NO_3)_2$ were dissolved in 100 mL of distilled water. 33 mL of the solution was combined with 3 g of the zeolite above. The pH was adjusted to 6 with 0.05 N nitric acid. The mixture was placed in an oven at 60° C. for twenty-four hours, swirling every hour for the first four hours. The mixture was decanted and the preceding procedure was repeated twice. The solids were washed five times with 60 mL of distilled water at room temperature for each wash. The solids were dried overnight at 90° C. and calcined by heating from room temperature to 300° C. at 1° C. per minute and maintaining the temperature at 300° C. for four hours.

Hydrogen Sulfide Pretreatment:

4.003 g of the formed catalyst above was loaded into a reactor, heated to 400° C. and swept with 50% hydrogen in nitrogen for four hours. The 50% hydrogen flow was replaced with 1% hydrogen sulfide (20 mL/minute) at 400° C. until hydrogen sulfide breakthrough was detected. The hydrogen sulfide stream was replaced with 50% hydrogen in nitrogen (40 mL/min) and treatment continued for one hour at 400° C.

COMPARATIVE EXAMPLE A

A zeolite containing only silica and alumina framework elements and a silica/alumina ratio of 150/1 (ZEOLYST CBV 15014G) was formed, ion-exchanged, calcined and pre-treated as in the zeolite synthesis, forming and ion exchanging of Example 1 above.

COMPARATIVE EXAMPLE B 15 g of ZSM-5 zeolite containing only silica and alumina (150:1) framework elements was mixed with a finely divided germanium oxide powder (0.30 g). This mixture was then formed, ion-exchanged, calcined, and pre-treated as in the zeolite synthesis, forming and ion exchange in Example 1 above.

COMPARATIVE EXAMPLE C 15 g of ZSM-5 zeolite containing only silica and alumina (150:1) framework elements was mixed with a finely divided germanium oxide powder (0.9 g). This mixture was then formed, ion-exchanged, calcined, and pre-treated as in as in the zeolite synthesis, forming and ion exchange in Example 1 above.

Catalyst Testing:

The catalysts were tested in a stainless steel tube using 15 psia propane diluted with nitrogen to 25 psia total. The weight hourly space velocities (WHSV) were 0.35 to 1.7 $h^{-1}$ depending on the activity of the catalyst employed. The products were analyzed by on-line sampling to a gas chromatograph where all hydrocarbon components with carbon numbers between 1 and 12 were quantitatively determined. Selectivities are expressed on the amount of propane converted; A9+=$C_9$–$C_{11}$ aromatics; BTX=benzene+toluene+xylene.

A catalyst according to Example 1 was tested for propane aromatization and gave the results shown in Table 1. BTX selectivity remained constant for over 100 hours of testing.

TABLE 1

(Catalyst from Example 1)
WHSV = 0.35 h$^{-1}$; Reaction T = 475° C.

| Time (h) | Conversion (%) | CH$_4$ (wt %) | C$_2$H$_6$ (wt %) | C$_4$H$_{10}$ (wt %) | A9+ (wt %) | BTX (wt %) |
|---|---|---|---|---|---|---|
| 3.5 | 37 | 2 | 24 | 11 | 6 | 56 |
| 12.5 | 34 | 2 | 24 | 13 | 5 | 56 |
| 24.5 | 33 | 2 | 24 | 13 | 4 | 56 |
| 36.5 | 32 | 2 | 24 | 14 | 4 | 55 |
| 48.5 | 33 | 2 | 24 | 14 | 4 | 56 |
| 60.5 | 33 | 2 | 24 | 14 | 3 | 56 |
| 72.5 | 32 | 2 | 24 | 14 | 3 | 56 |
| 84.5 | 31 | 2 | 24 | 14 | 3 | 56 |
| 96.5 | 31 | 2 | 24 | 14 | 3 | 56 |
| 112 | 30 | 2 | 24 | 14 | 3 | 56 |
| 137 | 32 | 2 | 23 | 14 | 3 | 57 |
| 146 | 31 | 2 | 23 | 15 | 3 | 56 |

A catalyst according to Comparative Example A was tested for propane aromatization and gave the results shown in Table 2. The selectivity did not remain constant over the first 100 hours.

TABLE 2

(Catalyst from Comparative Example A)
WHSV = 0.35 h$^{-1}$; Reaction T = 465° C.

| Time (h) | Conversion (%) | CH$_4$ (wt %) | C$_2$H$_6$ (wt %) | C$_4$H$_{10}$ (wt %) | A9+ (wt %) | BTX (wt %) |
|---|---|---|---|---|---|---|
| 3.5 | 39 | 2 | 23 | 12 | 8 | 54 |
| 12.5 | 35 | 2 | 26 | 15 | 6 | 50 |
| 23 | 37 | 2 | 30 | 15 | 6 | 46 |
| 35 | 38 | 2 | 32 | 16 | 5 | 43 |
| 47 | 37 | 2 | 33 | 17 | 6 | 41 |
| 59 | 35 | 2 | 34 | 17 | 5 | 40 |
| 71 | 37 | 2 | 35 | 18 | 5 | 38 |
| 83 | 37 | 2 | 36 | 18 | 5 | 38 |
| 95 | 36 | 2 | 36 | 18 | 5 | 37 |
| 107 | 35 | 2 | 36 | 19 | 5 | 36 |
| 119 | 34 | 2 | 36 | 19 | 5 | 36 |
| 131 | 33 | 2 | 36 | 19 | 5 | 36 |
| 146 | 33 | 2 | 37 | 19 | 5 | 36 |

A catalyst according to Comparative Example B was tested for propane aromatization and gave the results shown in Table 3. The selectivity did not remain constant.

TABLE 3

(Catalyst from Comparative Example B)
WHSV = 0.6 h$^{-1}$; Reaction T = 450° C.

| Time | Conversion | CH$_4$ | C$_2$H$_6$ | C$_4$H$_{10}$ | A9+ | BTX |
|---|---|---|---|---|---|---|
| 2 | 37 | 2 | 30 | 12 | 6 | 49 |
| 2.75 | 39 | 2 | 31 | 12 | 6 | 49 |
| 3.5 | 38 | 2 | 31 | 12 | 6 | 48 |
| 4.25 | 39 | 2 | 32 | 12 | 5 | 47 |
| 5 | 38 | 2 | 32 | 12 | 5 | 47 |
| 9.5 | 40 | 2 | 34 | 12 | 5 | 45 |
| 15.5 | 39 | 2 | 35 | 13 | 5 | 44 |
| 20 | 38 | 2 | 35 | 13 | 5 | 43 |
| 24.5 | 38 | 2 | 36 | 13 | 5 | 43 |
| 30.5 | 37 | 2 | 36 | 13 | 5 | 42 |
| 35 | 38 | 2 | 36 | 13 | 5 | 42 |
| 39.5 | 37 | 2 | 36 | 13 | 5 | 42 |

TABLE 3-continued (Catalyst from Comparative Example B)
WHSV = 0.6 h$^{-1}$; Reaction T = 450° C.

| Time | Conversion | CH$_4$ | C$_2$H$_6$ | C$_4$H$_{10}$ | A9+ | BTX |
|---|---|---|---|---|---|---|
| 45.5 | 37 | 2 | 37 | 13 | 5 | 42 |
| 47 | 37 | 2 | 36 | 13 | 5 | 42 |

A catalyst according to Comparative Example C was tested for propane aromatization and gave the results shown in Table 4. The selectivity did not remain constant.

TABLE 4

(Catalyst from Comparative Example C)
WHSV = 0.3 h$^{-1}$; Reaction T = 450° C.

| time | Conversion | CH$_4$ | C$_2$H$_6$ | C$_4$H$_{10}$ | A9+ | BTX |
|---|---|---|---|---|---|---|
| 3.2 | 46 | 4 | 42 | 9 | 0 | 45 |
| 5.2 | 46 | 4 | 43 | 10 | 0 | 43 |
| 9.8 | 45 | 4 | 44 | 10 | 0 | 42 |
| 15.2 | 35 | 3 | 41 | 15 | 0 | 41 |
| 19.8 | 35 | 3 | 41 | 15 | 0 | 41 |
| 25.2 | 34 | 3 | 41 | 15 | 0 | 40 |
| 30.5 | 34 | 3 | 42 | 15 | 0 | 40 |
| 39.8 | 34 | 3 | 41 | 15 | 0 | 40 |
| 49.2 | 34 | 3 | 42 | 15 | 0 | 40 |
| 75.2 | 33 | 3 | 42 | 15 | 0 | 40 |
| 99.2 | 33 | 3 | 42 | 15 | 0 | 40 |
| 125.8 | 32 | 3 | 42 | 15 | 0 | 39 |
| 149.2 | 31 | 3 | 42 | 15 | 0 | 39 |
| 175.8 | 31 | 3 | 42 | 15 | 0 | 40 |
| 199.2 | 31 | 3 | 42 | 15 | 0 | 39 |
| 249.2 | 29 | 3 | 41 | 16 | 0 | 39 |
| 292.5 | 28 | 3 | 41 | 16 | 0 | 39 |

As can be seen from the data above, while the percent conversion of all of the catalysts are comparable, the catalyst having aluminum-silicon-germanium zeolite on which platinum has been deposited (Example 1) has higher selectivity for benzene-toluene-xylene (BTX) which remained essentially constant for over 100 hours of operation. The catalysts which did not have germanium in the zeolite framework lost effectiveness for BTX selectivity over time.

A catalyst according to the present invention had an X-ray pattern diffraction pattern shown below where given values have been determined according to standard methods (Radiation: Cu—K-α(alpha), Wavelength: 1.54A).

TABLE 5

Main Powder XRD intensities for Ge-ZSM-5

| d-spacing[A] | Intensity |
|---|---|
| 11.15 | 40 |
| 10.04 | 33 |
| 9.77 | 12 |
| 6.38 | 13 |
| 4.27 | 19 |
| 3.85 | 100 |
| 3.77 | 22 |
| 3.72 | 42 |
| 3.66 | 35 |

The intensities shown are scaled in arbitrary units so that the most intense peak is 100. The peaks for Ge-ZSM-5 are shifted towards higher d-spacing values as compared to an Al-ZSM-5.

Numerous modifications and variations of the present invention are possible in light of the above teachings. It is to be understood that, within the scope of the appended claims, the invention may be practiced other than as specifically described.

What is claimed as new and desired to be secured by letter of Patent of the United States of America is:

1. A process for the aromatization of hydrocarbons comprising:
   a) contacting an alkane containing 2 to 6 carbon atoms per molecule with at least one catalyst containing an aluminum-silicon-germanium zeolite on which platinum has been deposited; and
   b) recovering the aromatic product.

2. The process of claim 1 wherein the silicon-germanium to aluminum atomic ratio is greater than 25:1.

3. The process of claim 1 wherein the silicon-germanium to aluminum atomic ratio in the range of from 45:1 to 250:1.

4. The process of claim 1 wherein the silicon-germanium to aluminum atomic ratio in the range of from 50:1 to 100:1.

5. The process of claim 1 wherein the silica to germania ratio is in the range of from 100:1 to 8:1.

6. The process of claim 1 wherein the silica to germania ratio is in the range of from 50:1 to 10:1.

7. The process of claim 1 wherein the silica to germania ratio is in the range of from 25:1 to 11:1.

8. The process of claim 1 wherein platinum is present in the range of from 0.05% to 3%.

9. The process of claim 1 wherein platinum is present in the range of from 0.2% to 2%.

10. The process of claim 1 wherein platinum is present in the range of from 0.2% to 1.5%.

11. The process of claim 1 wherein the contact between the alkane and the catalyst is at a space velocity in the range between 0.1 and 100 $h^{-1}$.

12. The process of claim 1 wherein the contact between the alkane and the catalyst is at a temperature in the range between 200 and 600° C.

13. The process of claim 1 wherein the contact between the alkane and the catalyst is at a pressure in the range between 5 and 215 psia.

14. The process of claim 1 wherein the zeolite has a MFI, FAU, TON, MFL, VPI, MEL, AEL, AFI, MWW or MOR structure.

15. The process of claim 1 wherein the catalyst additionally contains sulfur.

16. The process of claim 1 wherein the alkane additionally contains sulfur.

* * * * *

UNITED STATES PATENT AND TRADEMARK OFFICE
CERTIFICATE OF CORRECTION

PATENT NO. : 6,784,333 B2
APPLICATION NO. : 10/213313
DATED : August 31, 2004
INVENTOR(S) : Juttu et al.

It is certified that error appears in the above-identified patent and that said Letters Patent is hereby corrected as shown below:

Delete Figure 1, and substitute Attached Figure 1

Signed and Sealed this

Thirtieth Day of January, 2007

JON W. DUDAS
*Director of the United States Patent and Trademark Office*